(12) United States Patent
Gu (10) Patent No.: US 7,514,529 B2
(45) Date of Patent: Apr. 7, 2009

(54) PEPTIDE MIMOTOPES OF LIPOOLIGOSACCHARIDE FROM NONTYPEABLE HAEMOPHILUS INFLUENZAE AS VACCINES

(75) Inventor: Xin-Xing Gu, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 221 days.

(21) Appl. No.: 11/187,419

(22) Filed: Jul. 22, 2005

(65) Prior Publication Data

US 2006/0018919 A1   Jan. 26, 2006

Related U.S. Application Data

(63) Continuation of application No. PCT/US2004/001457, filed on Jan. 21, 2004.

(60) Provisional application No. 60/441,928, filed on Jan. 22, 2003.

(51) Int. Cl.
C07K 1/00 (2006.01)
C07K 2/00 (2006.01)

(52) U.S. Cl. ...................... 530/300; 530/350

(58) Field of Classification Search ................ 530/300, 530/350
See application file for complete search history.

(56) References Cited

U.S. PATENT DOCUMENTS 6,207,157 B1    3/2001   Gu et al.
6,562,958 B1 *  5/2003   Breton et al. .............. 536/23.7

FOREIGN PATENT DOCUMENTS

WO    WO/02/028888    * 11/2002

OTHER PUBLICATIONS

Charalambous et al, Mimotope vaccines, 2001, J Med Microbiol, vol. 50, pp. 937-939.*
Aoki, N. et al. 1996 "Antibody against synthetic multiple antigen peptides (MAP) of JC virus capsid protein (VP1) without cross reaction to BK virus: a diagnostic tool for progressive multifocal leukoencephalopathy." *Neurosci. Lett.* 205:111-114.
Avila, S.L. et al. 2001 "Immune responses to multiple antigen peptides containing T and B epitopes from *Plasmodium falciparum* circumsporozoite protein of Brazilian individuals naturally exposed to malaria." *Parasite Immunol.* 23:103-108.
Barenkamp, S.J. et al. 1990 "Development of serum bactericidal activity following nontypable *Haemophilus influenzae* acute otitis media." *Pediatr. Infect. Dis. J.* 9:333-339.
Berman, S. 1995 "Current concepts: otitis media in children." *N. Engl. J. Med.* 332:1560-1565.

Charalambous, B.M. et al. 2000 "Peptide mimics elicit antibody responses against the outer-membrane lipooligosaccharide of group B *Neisseria meningitidis.*" *FEMS Microbiol. Lett.* 191:45-50.
De Bolle, X. et al. 1999 "Antigenic properties of peptidic mimics for epitopes of the lipopolysaccharide from *Brucella.*" *J. Mol. Biol.* 294:181-191.
Demaria, T.F. et al. 1997 "Evaluation of the virulence of nontypeable *Haemophilus influenzae* lipooligosaccharide *htr*B and *rfa*D mutants in the chinchilla model of otitis media." *Infect. Immun.* 65:4431-4435.
Flesher, A.R. et al. 1978 "Characterization of lipopolysaccharide of *Haemophilus influenzae.*" *J. Infect. Dis.* 138:719-730.
Fleuridor, R. et al. 2001 "A cryptococcal capsular polysaccharide mimotope prolongs the survival of mice with *Cryptococcus neoformans* infection." *J. Immunol.* 166:1087-1096.
Gardsvoll, H. et al. 1998 "Selection of peptides that bind to plasminogen activator inhibitor 1 (PAI-1) using random peptide phage-display libraries." *FEBS Lett.* 431:170-174.
Giebink, G.S. 1989 "The microbiology of otitis media." *Pediatr. Infect. Dis. J.* 8:S18-S20.
Giebink G.S. et al. 2002 "Recent advances in otitis media. 7. Vaccine." *Ann. Otol. Rhinol. Laryngol.* 111:(Suppl. 188):82-94.
Glithero, A. et al. 1999 "Crystal structures of two H-2D$^b$/glycopeptide complexes suggest a molecular basis for CTL cross-reactivity." *Immunity.* 10:63-74.
Goodson, R.J. et al. 1994 "High-affinity urokinase receptor antagonists identified with bacteriophage peptide display." *PNAS USA* 91:7129-7133.
Grothaus, M.C. et al. 2000 "Selection of an immunogenic peptide mimic of the capsular polysaccharide of *Neisseria meningitidis* serogroup A using a peptide display library." *Vaccine* 18:1253-1263.
Gu, X.-X. et al. 1995 "Quantitation and biological properties of released and cell-bound lipooligosaccharide from nontypeable *Haemophilus influenzae.*" *Infect. Immun.* 63:4115-4120.
Gu, X.-X. et al. 1996 "Synthesis, characterization and immunological properties of detoxified lipooligosaccharide from nontypeable *Haemophilus influenzae* conjugated to proteins." *Infect. Immun.* 64:4047-4053.
Gu, X.-X. et al. 1997 "Detoxified lipooligosaccharide from nontypeable *Haemophilus influenzae* conjugated to proteins confers protection against otitis media in chinchillas." *Infect. Immun.* 65:4488-4493.
Gulati, S. et al. 1996 "Experimental immunization with a monoclonal anti-idiotype antibody that mimics the *Neisseria gonorrhoeae* lipooligosaccharide epitope 2C7." *J. Infect. Dis.* 174:1238-1248.
Harris, S.L. et al. 1997 "Exploring the basis of peptide-carbohydrate crossreactivity: evidence for discrimination by peptides between closely related anti-carbohydrate antibodies." *PNAS USA* 94:2454-2459.

(Continued)

*Primary Examiner*—Mark Navarro
(74) *Attorney, Agent, or Firm*—Knobbe, Martens, Olson & Bear, LLP (57) ABSTRACT

The present invention relates to peptide mimotopes of lipooligosaccharide from nontypeable Haemophilus influenzae as vaccines.

17 Claims, 2 Drawing Sheets

OTHER PUBLICATIONS

Hoess, R. et al. 1993 "Identification of a peptide which binds to the carbohydrate-specific monoclonal antibody B3." *Gene* 128:43-49.

Hogrefe, H.H. et al. 1993 "A bacteriophage lambda vector for the cloning and expression of immunoglobulin Fab fragments on the surface of filamentous phage." *Gene* 128:119-126.

Hou, Y. et al. 2003 "Development of Peptide Mimotopes of lipooligosaccharide from nontypeable *Haemophilus influenzae* as vaccine candidates" *J. Immunol.* 170:4373-4379.

Hu, W.G. et al. 2000 "An aerosol challenge mouse model for *Moraxella catarrhalis.*" *Vaccine* 18:799-804.

Hufton, S.E. et al. 1999 "Phage display of cDNA repertoires: the pVI display system and its applications for the selection of immunogenic ligands." *J. Immunol. Methods* 231:39-51.

Iniguez, P. et al. 1998 "Screening of horse polyclonal antibodies with a random peptide library displayed on phage: identification of ligands used as antigens in an ELISA test to detect the presence of antibodies to equine arteritis virus." *J. Virol. Methods* 73:175-183.

Jouault, T. et al. 2001. "Peptides that mimic *Candida albicans*-derived β-1,2-linked mannosides." *Glycobiology* 11:693-701.

Klein, J.O. et al. 1992 "New concepts in otitis media: results of investigations of The Greater Boston Otitis Media Study Group." *Adv. Pediatr.* 39:127-157.

Lesinski, G.B. et al. 2001 "A DNA vaccine encoding a peptide mimic of *Streptococcus pneumoniae* serotype 4 capsular polysaccharide induces specific anti-carbohydrate antibodies in Balb/c mice." *Vaccine* 19:1717-1726.

Lowman, H.B. et al. 1991 "Selecting high-affinity binding proteins by monovalent phage display." *Biochemistry* 30:10832-10838.

Marussig, M. et al. 1997 "Linear and multiple antigen peptides containing defined T and B epitopes of the *Plasmodium yoelii* circumsporozoite protein: antibody-mediated protection and boosting by sporozoite infection." *Int. Immunol.* 9:1817-1824.

McGehee, J.L. et al. 1989 "Effect of primary immunization on pulmonary clearance of nontypeable *Haemophilus influenzae.*" *Am. J. Respir. Cell Mol. Biol.* 1:201-210.

Moe, G.R. et al. 1999 "Molecular mimetics of polysaccharide epitopes as vaccine candidates for prevention of *Neisseria meningitidis* serogroup B disease." *FEMS Immunol. Med. Microbiol.* 26:209-226.

Monzavi-Karbassi, B. et al. 2002 "Peptide mimotopes as surrogate antigens of carbohydrates in vaccine discovery." *Trends Biotechnol.* 20:207-214.

Murphy, T.F. et al. 1987 "Nontypeable *Haemophilus influenzae*: a review of clinical aspects, surface antigens, and the human immune response to infection." *Rev. Infect. Dis.* 9:-15.

Musher, D.M. et al. 1983 "Pneumonia and acute febrile tracheobronchitis due to *Haemophilus influenzae.*" *Ann. Intern. Med.* 99:444-450.

Odermatt, A. et al. 2001 "Identification of receptor ligands by screening phage-display peptide libraries ex vivo on microdissected kidney tubules." *J. Am. Soc. Nephrol.* 12:308-316.

Oldenburg, K.R. et al. 1992 "Peptide ligands for a sugar-binding protein isolated from a random peptide library." *PNAS USA* 89:5393-5397.

Oleksiewicz, M.B. et al. 2001 "Epitope mapping porcine reproductive and respiratory syndrome virus by phage display: the nsp2 fragment of the replicase polyprotein contains a cluster of B-cell epitopes." *J. Virol.* 75:3277-3290.

Phalipon, A. et al. 1997 "Induction of anti-carbohydrate antibodies by phage library-selected peptide mimics." *Eur. J. Immunol.* 27:2620-2625.

Pincus, S.H. et al. 1998 "Peptides that mimic the group B streptococcal type III capsular polysaccharide antigen." *J. Immunol.* 160:293-298.

Schreiber, J.R. 1993 "Anti-idiotype vaccines for immunity to bacterial polysaccharides: induction of functional antibodies to polysaccharide antigens of *Pseudomonas aeruginosa.*" *Springer Semin. Immunopathol.* 15:235-246.

Scott, J.K. et al. 1990 "Searching for peptide ligands with an epitope library." *Science* 249:386-390.

Scott, J.K. et al. 1992 "A family of concanavalin A-binding peptides from a hexapeptide epitope library." *PNAS USA* 89:5398-5402.

Senpuku, H. et al. 1996 "Immunogenicity of peptides coupled with multiple T-cell epitopes of a surface protein antigen of *Streptococcus mutans.*" *Immunology* 88:275-283.

Smith, G.P. 1991 "Surface presentation of protein epitopes using bacteriophage expression systems." *Curr. Opin. Biotechnol.* 2:668-673.

Sun, J. et al. 2000 "Biological activities of antibodies elicited by lipooligosaccharide based-conjugate vaccines of nontypeable *Haemophilus influenzae* in an otitis media model." *Vaccine* 18:1264-1272.

Szardenings, M. et al. 1997 "Phage display selection on whole cells yields a peptide specific for melanocortin receptor 1." *J. Biol. Chem.* 272:27943-27948.

Ueyama, T. et al. 1999 "Identification of common lipooligosaccharide types in isolates from patients with otitis media by monoclonal antibodies against nontypeable *Haemophilus influenzae* 9274." *Clin. Diagn. Lab. Immunol.* 6:96-100.

Valadon, P. et al. 1996 "Peptide libraries define the fine specificity of anti-polysaccharide antibodies to *Cryptococcus neoformans.*" *J. Mol. Biol.* 261:11-22.

Valadon, P. et al. 1998 "Aspects of antigen mimicry revealed by immunization with a peptide mimetic of *Cryptococcus neoformans* polysaccharide." *J. Immunol.* 161:1829-1836.

Vest Hansen, N. et al. 2001 "Phage display of peptide/major histocompatibility class I complexes." *Eur. J. Immunol.* 31:32-38.

Westerink, M.A. et al. 1995 "Peptide mimicry of the meningococcal group C capsular polysaccharide." *PNAS USA* 92:4021-4025.

Yip, Y.L. et al. 1999 "Epitope discovery using monoclonal antibodies and phage peptide libraries." *Comb. Chem. High Throughput Screening* 2:125-138.

Young, A. et al. 1997 "The three-dimensional structures of a polysaccharide binding antibody to *Cryptococcus neoformans* and its complex with a peptide from a phage display library: implications for the identification of peptide mimotopes." *J. Mol. Biol.* 274:622-634.

Zhang, H. et al. 1997 "Peptide epitopes recognized by a human anti-cryptococcal glucuronoxylomannan antibody." *Infect. Immun.* 65:1158-1164.

Zhu, Z. et al. 2001 "Identification of epitopes of trichosanthin by phage peptide library." *Biochem. Biophys. Res. Commun.* 282:921-927.

\* cited by examiner

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: consensus frame of a synthetic peptide
<220> FEATURE:
<221> NAME/KEY: VARIANT
<222> LOCATION: 9
<223> OTHER INFORMATION: Xaa = Proline or Serine
<220> FEATURE:
```

```
<221> NAME/KEY: VARIANT
<222> LOCATION: 4, 5, 6, 7, 8, 10, 11, 12
<223> OTHER INFORMATION: Xaa = Any Amino Acid

<400> SEQUENCE: 1

Asn Met Met Xaa Xaa Xaa Xaa Xaa Xaa Xaa Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic peptide

<400> SEQUENCE: 2

Asn Met Met Arg Phe Thr Ser Gln Pro Pro Asn Asn
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Asn Met Met Asn Tyr Ile Met Asp Pro Arg Thr His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic peptide

<400> SEQUENCE: 4

Asn Met Met Lys Tyr Ile Ser Pro Pro Ile Phe Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthetic peptide

<400> SEQUENCE: 5

Asn Met Met Arg Phe Thr Glu Leu Ser Thr Pro Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic peptide

<400> SEQUENCE: 6

Thr Gln Ala Arg Ala Thr Pro Phe Gln Ser Phe Thr
1               5                   10

<210> SEQ ID NO 7
<211> LENGTH: 12
<212> TYPE: PRT
<213> ORGANISM: Artificial Sequence
```

```
<220> FEATURE:
<223> OTHER INFORMATION: synthetic peptide

<400> SEQUENCE: 7

Ser Asp Thr Lys Leu Thr Thr Ser Ser Lys Trp Val
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

Lys Pro Phe His Ser His Thr Gly Ala Thr Thr Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic peptide

<400> SEQUENCE: 9

Ala Tyr Ser Pro Pro Thr Pro Ala Glu Ala Pro Ile
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic peptide

<400> SEQUENCE: 10

Thr Leu Ala His His Lys Lys Pro Trp Ile Leu Arg
1               5                   10

<210> SEQ ID NO 11
<211> LENGTH: 5
<212> TYPE: PRT
<213> ORGANISM: Artificial Sequence
<220> FEATURE:
<223> OTHER INFORMATION: synthetic peptide linker

<400> SEQUENCE: 11

Gly Gly Gly Ser Cys
1               5
```

PEPTIDE MIMOTOPES OF LIPOOLIGOSACCHARIDE FROM NONTYPEABLE HAEMOPHILUS INFLUENZAE AS VACCINES

RELATED APPLICATIONS

This application is a continuation of International Patent Application No. PCT/US2004/001457 filed Jan. 21, 2004, designating the U.S. and published in English on Aug. 5, 2004 as WO 2004/065409, which claims the benefit of U.S. Provisional Application No. 60/441,928 filed Jan. 22, 2003, both of which are hereby expressly incorporated by reference in their entireties.

FIELD OF THE INVENTION

The present invention relates to peptide mimotopes of lipooligosaccharide from nontypeable Haemophilus influenzae as vaccines.

BACKGROUND OF THE INVENTION

Nontypeable Haemophilus influenzae (NTHi) is a common pathogen that causes otitis media (OM) in children and lower respiratory tract infections in adults, especially those with chronic obstructive pulmonary diseases (Klein et al. 1992 *Adv Pediatr* 39:127; Murphy and Apicella. 1987 *Rev Infect Dis* 9:1; Musher et al. 1983 *Ann Intern Med* 99:344). Prevention of NTHi infections is important because OM is a major cause of conductive hearing impairment in children who are at the critical age for speech and language development (Giebink 1989 *Pediatr Infect Dis J* 8:S18). The exacerbation of chronic obstructive pulmonary diseases in elderly is life threatening, the fourth leading cause of death in the United States. In addition, repeated or inappropriate antibiotic treatment of OM and other respiratory diseases contributes to the emergence of antibiotic-resistant strains (Berman 1995 *N Engl J Med* 332:1560). Therefore, there is an urgent need to develop prophylactic vaccines to prevent these NTHi-caused diseases.

In the past years, significant progresses have been made toward identifying vaccine candidates based on NTHi surface antigens such as outer membrane proteins and lipooligosaccharide (LOS). These antigens are potential targets for humoral immunity and bactericidal antibodies that appear to be important in protecting against NTHi OM (Geibink et al. 2002 *Ann Otol Rhinol Laryngol* 111:S188: 82). Our strategy is to use LOS as a vaccine component, since NTHi does not have a detectable capsular polysaccharide and its LOS is both a virulence factor (DeMaria et al. 1997 *Infect Immun* 65:4431; Flesher and Insel 1978 *J Infect Dis* 138:719; Gu et al. 1995 *Infect Immun* 63:4115) and a potential protective surface antigen (Barenkamp and Border 1990 *Pediatric Infect Dis J* 9:333; Ueyama et al. 1999 *Clin Diagn Lab Immunol* 6:96; McGehee et al. 1989 *Am J Respir Cell Mol Biol* 1:201). Previously, we chemically conjugated a relatively conserved detoxified LOS to proteins to form vaccines (Gu et al. 1996 *Infect Immun* 64:4047). These conjugates were immunogenic in mice and rabbits and conferred T cell-dependent immunological protection against experimental OM in chinchillas (Gu et al. 1997 *Infect Immun* 65:4488; Sun et al. 2000. *Vaccine* 18:1264).

The LOS can also be converted into a nontoxic T cell-dependent antigen through the use of anti-idiotype antibodies (Schreiber 1993 *Springer Semin Immunopathol* 15:235; Gulati et al. 1996 *J Infect Dis* 174:1238) or peptides that mimic the LOS (Phalipon et al. 1997 *Eur J Immunol* 27:2620; Charalambous and Feavers. 1998 *Abstracts of the Eleventh International Pathogenic Neisseria Conference.* Eds: Nassif et al. p.186. Editions E.D.K., Paris, France.). A strategy based on the mimicry of saccharide antigens by anti-idiotype antibodies is difficult and time-consuming. Recently, phage-display has been used to identify ligands for a variety of target molecules by an affinity selection process called biopanning (Goodson et al. 1994 *PNAS USA* 91:7129; Szardenings et al. 1997 *J Biol Chem* 272:27943; Iniguez et al. 1998 *J Virol Methods* 73:175; Hogrefe et al. 1993 *Gene* 128:119; Scott and Smith 1990 *Science* 249:386; Lowman et al. 1991 *Biochemistry* 30:10832; Smith 1991 *Curr Opin Biotechnol* 2:668). Random peptide libraries displayed on bacteriophage outer proteins have been used successfully to screen for peptides that bind antibodies as well as non-antibody molecules (Pincus et al. 1998 *J Immunol* 160:293; Valadon et al. 1996 *J Mol Biol* 261:11; Moe et al. 1999 *FEMS Immunol Med Microbiol* 26:209; Grothaus et al. 2000 *Vaccine* 18:1253; Lesinski et al. 2001 *Vaccine* 19:1717; Zhang et al. 1997 *Infect Immun* 65:1158; Yip and Ward 1999 *Comb Chem High Throughput Screen* 2:125; Hufton et al. 1999 *J Immunol Method* 231:39; Gardsvoll et al. 1998 *FEBS Lett* 431:170; Vest Hansen et al. 2001 *Eur J Immunol* 31:32; Odermatt et al. 2001 *J Am Soc Nephrol* 12:308). These studies allow investigators to map the target sequences for monoclonal or polyclonal antibodies that recognize both linear and conformational epitopes.

Libraries have been used to identify peptides that mimic the carbohydrate structures of bacteria, cancer cells, or viruses (Pincus et al. 1998 *J Immunol* 160:293; Valadon et al. 1996 *J Mol Biol* 261:11; Moe et al. 1999 *FEMS Immunol Med Microbiol* 26:209; Grothaus et al. 2000 *Vaccine* 18:1253; Oldenburg et al. 1992 *PNAS USA* 89:5393; Scott et al. 1992 *PNAS USA* 89:5398; Zhu et al. 2001 *Biochem Biophys Res Commun* 282:921; Oleksiewicz et al. 2001 *J Virol* 75:3277). In the case of bacteria, several studies have reported success in isolating peptide mimetics that elicit an immune response against native bacterial saccharide structures in animal models. A study by Phalipon et al. (1997 *Eur J Immunol* 27:2620) was an early example of immunogenic mimicry of bacterial saccharides by phage-displayed peptides. They used two monoclonal antibodies specific for the O-antigen part of *Shigella flexneri* serotype 5a LPS to screen two phage-display nonapeptide libraries. Some of the selected phage clones could induce specific anti-O-antigen antibodies in mice. The immune response selectively recognized the corresponding bacterial strains. Using a similar method, Pincus et al. (1998 *J Immunol* 160:293) located peptides that bind to monoclonal antibodies specific for type 3 capsular polysaccharide of group B streptococci (GBS). The latter peptide specifically blocked the binding of anti-GBS antibodies to GBS and elicited an anti-GBS antibody response in mice when conjugated to protein carriers. Instead of using peptides from phage display library, Westerink et al. (1995 *PNAS USA* 92:4021) developed a peptide derived from anti-idiotype monoclonal antibody. The latter peptide elicited a protective antibody of meningococcal group C polysaccharide. Table I summarizes reports of peptide mimetics of bacterial or fungal carbohydrate structures. These studies reveal that some of the mimic peptides only show antigenicity in vitro while others can be antigenic and immunogenic in vivo, indicating a new strategy for selection of immunogens for the development of anti-saccharide vaccines.

TABLE I

Peptide mimetics of bacterial (fungal) capsular polysaccharide (CPS), lipopolysaccharide (LPS) or lipooligosaccharides (LOS)

| Carbohydrate | Mimetic Peptide | Features | Reference |
| --- | --- | --- | --- |
| *Brucella* LPS | 6–16 mer | Elicits weak anti-LOS antibody | De Bolle et al. 1999 J Mol Biol 294: 181 |
| *Candida albicans* β-1,2-mannosides CPS | 7 mer | Elicits anti-β-1,2-mannoside antibody | Jouault et al. 2001 Glyco-biology 11: 693 |
| Cryptococcal glucuronoxylomannan CPS | 6, 10 mer | Peptides are good antigenic mimetics but poor immunogenic mimetics Peptides protect against challenge | Valadon et al. 1996 J Mol Biol 261: 11; Valadon et al. 1998 J Immunol 161: 1829 Zhang et al. 1997 Infect Immun 65: 1158 Fleuridor et al., 2001 J Immunol 166: 1087 |
| Group A streptococcal CPS | 6, 15 mer | Mab binding to peptide mimetics different than binding to CPS | Harris et al. 1997 PNAS USA 94: 2454 |
| Group B streptococcal Type III CPS | 12 mer | Elicits anti-CPS antibody | Pincus et al. 1998 J Immunol 160: 293 |
| Meningococcal group A CPS | 15 mer | Elicits anti-CPS antibody | Grothaus et al., 2000 Vaccine 18: 1253 |
| Meningococcal group B CPS | 6, 8 mer | Peptides are good antigenic mimetics but poor immunogenic mimetics | Moe et al. 1999 FEMS Immunol Med Microbiol 26: 209 |
| Meningococcal group C CPS | V regions of mAb | Elicits protective anti-CPS antibody peptide derived from anti-Id Mab | Westerink et al. 1995 PNAS USA 92: 4021 |
| Meningococcal LOS | 7 mer | Elicits weak to medium anti-LOS antibody | Charalambous &Feavers 2000 FEMS Microbiol Lett 191: 45 |
| Pneumococcal Serotype 4 CPS | 15 mer | Elicits anti-CPS antibody | Lesinski et al. 2001 Vaccine 19: 1717 |
| *Shigella flexneri* serotype 5a LPS | 9 mer | Two of 19 peptides identified elicit anti-LOS antibodies | Phalipon et al. 1997 Eur J Immunol 27: 2620 |

Segue to Invention

In this study, we have used a phage display peptide library and, a rabbit bactericidal polyclonal antibody specific for NTHi LOS to screen for a peptide mimic of NTHi LOS. Three peptides selected from the library were synthesized and conjugated to keyhole limpet hemosyanin (KLH). Immunogenicity of the peptide conjugates was evaluated in rabbits and the protective property of the conjugate-induced rabbit sera was further evaluated in a mouse challenge model.

SUMMARY OF THE INVENTION

The present invention relates to peptide mimotopes of lipooligosaccharide from nontypeable Haemophilus influenzae as vaccines.

BRIEF DESCRIPTION OF THE DRAWINGS

FIG. 1. Binding reactivity of synthetic peptide conjugates to the target rabbit anti-LOS antibody (A) or a mouse anti-LOS antibody 6347C11 (B) by ELISA. Antigenicity of the synthetic peptide conjugates was examined in ELISA using three synthetic peptide conjugates or a carrier KLH as coating antigens, followed by incubation with either the target anti-LOS antibody or the monoclonal anti-LOS antibody. The binding reactivity of the synthetic peptides to both antibodies was evaluated by average $OD_{405}$ values of each duplicate sample after incubation with a goat anti-rabbit IgG (or anti-mouse IgM) alkaline phosphatase conjugate, and then addition of a substrate. Conjugates 1, 2, and 3 were synthesized from peptides 2, 3, and 4.

FIG. 2. Rabbit serum antibody responses elicited by synthetic peptide conjugates. New Zealand White female rabbits, two for each group, were subcutaneously immunized with 500 μg of each conjugate (approximately 100 μg of peptide content), mixed with complete Freund adjuvant for the first injection, or incomplete Freund adjuvant for three boosters with 20-day intervals. A control rabbit immunized with 500 μg of KLH analog with the previously described adjuvants was also included. Blood samples were collected 10 days after the last booster to detect serum IgG antibodies against LOS by ELISA using NTHi 9274 LOS as a coating antigen. Rabbit anti-LOS IgG antibody levels were expressed as reciprocal of ELISA titers.

BRIEF DESCRIPTION OF SEQUENCES

| SEQ. ID. NO. | Sequence | Description |
| --- | --- | --- |
| 1 | NMMXXXXXP(S)XXX | Consensus frame |
| 2 | NMMRFTSQPPNN | Peptide 1 |

-continued

| SEQ. ID. NO. | Sequence | Description |
|---|---|---|
| 3 | NMMNYIMDPRTH | Peptide 2 |
| 4 | NMMKYISPPIFL | Peptide 3 |
| 5 | NMMRFTELSTPS | Peptide 4 |

DETAILED DESCRIPTION OF THE PREFERRED EMBODIMENT

Nontypeable Haemophilus influenzae (NTHi) is a common cause of otitis media in children and lower respiratory tract diseases in adults. So far there is no effective vaccine against NTHi. A major surface-exposed component of NTHi, lipooligosaccharide (LOS), is a virulence factor as well as a potential protective antigen. LOS is too toxic to be administered in humans. However, detoxified LOS is a T cell-independent small molecule and is poorly immunogenic in vivo, so we converted LOS into a nontoxic T cell-dependent antigen through the use of peptides that mimic the LOS by screening a phage display peptide library with a rabbit antibody specific for NTHi LOS. Fifty-six phage clones were found to share LOS mimicry molecules. Among them, 22 clones were subjected to DNA sequencing, and four consensus sequences were identified as NMMRFTSQPPNN (SEQ ID NO: 2), NMMNYIMDPRTH (SEQ ID NO: 3), NMMKYISPPIFL (SEQ ID NO: 4) and NMMRFTELSTPS (SEQ ID NO: 5). Three out of the four synthetic peptides showed strong binding reactivity to the anti-LOS antibody and also a mouse bactericidal monoclonal anti-LOS antibody in vitro, and elicited specific serum anti-LOS antibodies in rabbits (27 to 81-fold) after conjugation with keyhole limpet hemosyanin. Passive immunization with the rabbit antisera resulted in a significantly enhanced pulmonary bacterial clearance in a mouse model. The enhanced bacterial clearance was eliminated if the rabbit serum was pre-absorbed with NTHi LOS. These data indicate that the peptide mimotopes of LOS that we have identified embody valuable components of peptide vaccines against NTHi.

A Method of Isolating a Mimotope which Immunologically Mimics NTHi LOS and the use thereof in a Vaccine The present invention relates to a method of isolating a mimotope which immunologically mimics lipooligosaccharide from nontypeable Haemophilus influenzae (NTHi LOS), comprising the steps of:
(a) contacting a phage-display library, having phage, with one or more antibodies specific for NTHi LOS;
(b) isolating one or more phage, having a displayed peptide, which bind one or more of the antibodies; and
(c) selecting, for at least one said phage isolated in step (b), the peptide or peptide fragment to which the antibodies have bound.

A peptide which "immunologically mimics NTHi LOS" is a substance that elicits an antibody response against NTHi LOS. The peptide is preferably at least three amino acids, although peptides of any length are within the scope of the invention.

"Contacting", as used herein, refers to incubation for a sufficient period of time to permit antibody/antigen binding to occur, as can be easily measured by methods routine in the art.

"Phage display library", as used herein, refers to a multiplicity of phage which express random amino acid sequences of less than 100 amino acids in length, less than 75 amino acids, less than 50 amino acids, and particularly within the range of 3 to 25 amino acids at a location which may be bound by an antibody.

Particularly preferred in the practice of this invention is a phage display library produced by the method of Burritt et al. (Burritt, J. B. et al. 1996 *Anal Biochem* 238:1). Phage has the usual meaning it is given by one of ordinary skill in the art. (See, for example, Sambrook, J. E. et al. 1989 *Molecular Cloning: a Laboratory Manual* Cold Spring Harbor, N.Y. Cold Spring Harbor Laboratory)

The phrase "antibodies specific for NTHi LOS" refers to monoclonal or polyclonal antibodies which bind the NTHi LOS with an affinity greater than the average unselective affinity which these antibodies show for substances structurally unrelated to NTHi LOS. Antibodies of all isotypes, i.e., IgG, IgA, IgM, IgD, and IgE, may be used.

The phrase "isolating one or more phage . . . which bind one or more of the antibodies" means physically removing from the phage display library phage that bind the antibody with greater affinity than that between the antibody and a structurally unrelated antigen.

Although any technique for isolation may be used in the practice of the invention, a particular method is affinity purification, which is well known in the art. A particular means of isolating phage from the phage display library is to first preabsorb the library with antibodies specific for an antigen structurally unrelated to NTHi LOS. Following preabsorption, the library is incubated with one or more antibodies specific for NTHi LOS. Following this incubation, the unbound phage are washed away, and the bound phage eluted. Next, the eluated pools are amplified, most preferably in an *E. coli* strain. Following elution, each pool is reapplied to the column, and the same incubation and washing procedure employed, eluting (in the end) with the same substance used to generate the original pool. This process is repeated for each pool, most preferably three times. Finally, phage are tested for binding to the selecting antibody. Phage which pass this final round are cloned, amplified to high titer, and purified by precipitation.

"Displayed peptide" refers to peptides having an amino-acid sequence of less than 100 amino acids in length, less than 75 amino acids, less than 50 amino acids, and particularly within the range of 3 to 25 amino acids which varies randomly between each of the individual phage which make up the phage display library.

Once the peptides are isolated by this process, they may be used in a vaccine. Thus, the present invention provides a component for a vaccine against nontypeable Haemophilus influenzae (NTHi), which comprises a mimotope which immunologically mimics lipooligosaccharide from nontypeable Haemophilus influenzae (NTHi LOS). The mimotope preferable binds one or more antibodies specific for NTHi LOS. The mimotope preferably comprises a peptide epitope which may be obtained by:
(a) contacting a phage-display library, having phage, with one or more antibodies specific for NTHi LOS;
(b) isolating one or more phage, having a displayed peptide, which bind one or more of the antibodies; and
(c) selecting, for at least one said phage isolated in step 3, the peptide or peptide fragment to which the antibodies have bound.

Typically, a peptide library such as a dodecapeptide library preferably-containing all possible amino acid sequences should be used to give the greatest diversity of potential epitopes against which antigenic cross-reactivity with the antibody can be assessed. Typically, a random peptide library of this nature is used.

In the present invention it was found that a dodecapeptide library was conveniently challenged with the relevant antibody and the following peptide sequences were found to be particularly useful:

```
NMMRFTSQPPNN,      (SEQ. ID. NO:2)
NMMNYIMDPRTH,      (SEQ. ID. NO:3)
NMMKYISPPIFL,      (SEQ. ID. NO:4)
and NMMRFTELSTPS.  (SEQ. ID. NO:5)
```

According to the present invention, the peptide epitope may comprise a subsequence of any one of the dodecapeptide sequences or may be present in a longer peptide incorporating any one of the above dodecapeptides or sub-sequences therefrom.

In a further embodiment, the mimotope may comprise an oligopeptide which is structurally more constrained than a linear form of the oligopeptide. An unsubstituted linear oligopeptide such as present free in solution would normally be able to assume a large number of different conformations. In contrast, an oligopeptide which is structurally constrained, perhaps by having one or usually two or more substituents which reduce in number the possible conformations which it can assume, is also within the scope of the present invention.

Substituents such as covalent linkages to further peptide chains or intramolecular linkages will structurally constrain the oligopeptide. For example, the oligopeptide may form part of the primary structure of a larger polypeptide containing the amino acid sequence of the oligopeptide. Preferably, the oligopeptide comprises a cyclic peptide, as discussed in further detail below.

Other substituents include covalent linkages to other moieties such as macromolecular structures including biological and nonbiological structures. Examples of biological structures include carrier proteins such as those described below for enhancing the immunogenicity of the mimotope. Examples of non-biological structures include lipid vesicles such as micelles and the like.

In another embodiment, the oligopeptide comprises a cyclic peptide. Use of a cyclic peptide is thought to have advantages compared to a linear peptide because the cyclic peptide is able to assume fewer conformations that the linear peptide and is therefore structurally more constrained. Typically, the cyclic peptide comprises a cyclised portion, which cyclised portion preferably comprises an amino acid sequence, the terminal amino acids of which are linked together by a covalent bond. The covalent bond is conveniently a disulphide bridge, such as found between cysteine residues. The cyclised portion conveniently comprises a dodecapeptide and this dodecapeptide can conveniently form part of the amino acid sequence which is flanked by the amino acids which are linked by the covalent bond to form the cyclised portion.

It is preferred that the docecapeptide has the sequence NMMXXXXXP(S)XXX (SEQ. ID. NO: 1), wherein each X is the same or different and is an amino acid, preferably a naturally-occurring amino acid. Preferably the fifth position contains an aromatic group, such as phenylalanine or tyrosine.

In addition to the above linear and cyclic peptides, it is possible to use, instead of peptides based on naturally-occurring L-amino acids, peptides comprising corresponding D-amino acids with the sequence of amino acids running in reverse order. These D-amino acid based peptides are sometimes termed retropeptides and can be more immunogenic and less prone to proteolysis than their L-amino acid counterparts.

In another embodiment, a carrier is conjugated to the mimotope to enhance the immunogenicity thereof. A number of carriers are known for this purpose, including various immunogenic protein-based carriers such as albumin (such as bovine serum albumin (BSA)), keyhole limpet hemocyanin (KLH), ovalbumin (OVA), tetanus toxoid (TT), high-molecular weight proteins (HMP) from nontypeable Haemophilus influenzae (Barenkamp 1996 *Infect Immun* 64:1246), diphtheria toxoid, or bacterial outer membrane protein, all of which may be obtained from biochemical or pharmaceutical supply companies or prepared by standard methodology (Cruse, J. M. et al. 1989 *Contrib Microbiol Immunol* 10:1).

The component for the vaccine may incorporate a plurality of mimotopes of NTHi LOS in which each mimotope is the same or different. By having more than one mimotope, the immunogenicity of the component may be enhanced. The plurality of mimotopes may be conjugated together, for example using a polylysine to which each mimotope is conjugated.

In another embodiment, a mimotope may be engineered to contain additional structures, including T helper cell epitopes and built-in adjuvants.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Martin, E. W., *Remington's Pharmaceutical Sciences*, specifically incorporated herein by reference. These carriers can also contain adjuvants, including but not limited to alum, aluminum compounds (phosphate and hydroxide), and muramyl dipeptide derivatives.

The invention also relates to the treatment of a patient by administration of an immunostimulatory amount of the vaccine. Patient refers to any subject for whom the treatment may be beneficial and includes mammals, especially humans. An immunostimulatory amount refers to that amount of vaccine that is able to stimulate the immune response of the patient for the prevention, amelioration, or treatment of diseases.

The vaccine of the invention may be administered by any route, but is preferably administered topically, mucosally or orally. Other methods of administration will be familiar to those of ordinary skill in the art, including intravenous, intramuscular, intraperitoneal, intracorporeal, intrarticular, intrathecal, intravaginal, intranasal, oral and subcutaneous injections.

In addition, once a mimetic peptide of the invention is identified and sequenced, DNA encoding the amino acid sequence of the peptide can itself be used as a vaccine. Techniques for preparing the specified DNA coding regions within suitable DNA delivery vectors are well established. DNA can be directly introduced into the host organism, e.g., by injection (See International Publication NO. WO 90/11092; and Wolff et al. 1990 *Science* 247:1465).

Specificity of a Target Anti-LOS Antibody

A rabbit antiserum elicited by NTHi 9274 dLOS-TT conjugate was purified through an LOS affinity column. The binding specificity of anti-LOS antibody to NTHi 9274 LOS was analyzed by an LOS ELISA. The rabbit anti-LOS antibody bound strongly to the 9274 LOS with an OD value of 1.57, a 17-fold greater binding than for an irrelevant rabbit antibody with an OD value of 0.09. This rabbit anti-LOS antibody was used as a target antibody for each of the following biopanning rounds.

Screening for Positive Clones by the Biopanning Procedure

A modified biopanning protocol was performed to screen a phage display peptide library for positive clones with the target anti-LOS antibody. After three bio-panning rounds, 56 positive phage clones were identified from 108 individual clones (Table II). These clones showed specific binding to the target anti-LOS antibody with the ELISA OD values of 2- to 1,510-fold higher than that of an irrelevant antibody. Twenty-two positive clones, most with high ELISA values, from different bio-panning rounds were selected for DNA sequencing. As comparison, four negative clones were also selected randomly for DNA sequencing. Twenty-two peptide sequences were deduced and analyzed. Four consensus sequences with a frame of NMMXXXXXP(S)XXX (SEQ ID NO:1) were identified in Table III. Each sequence also shows a consensus aromatic group (F or Y) at the fifth position of the N-terminus. As controls, no consensus peptide sequence was found from negative clones, TQARATPFQSFT (SEQ ID NO: 6), SDTKLTTSSKWV (SEQ ID NO: 7), KPFHSHTGATTP (SEQ ID NO: 8), and AYSPPTPAEAPI (SEQ ID NO: 9).

TABLE II

Positive Clones and their ELISA binding reactivity to a target anti LOS antibody

| Clone No. | Fold rise of ELISA value[a] | Clone No. | Fold rise of ELISA value | Clone No. | Fold rise of ELISA value |
|---|---|---|---|---|---|
| 1-8 | 208 | 2-12 | 644 | 2-16 | 21 |
| 1-34 | 196 | 2-32 | 266 | 2-26 | 21 |
| 1-25 | 86 | 2-28 | 214 | 2-13 | 20 |
| 1-23 | 82 | 2-10 | 146 | 2-15 | 1510 |
| 1-32 | 63 | 2-21 | 131 | 2-9 | 1340 |
| 1-29 | 61 | 2-5 | 131 | 3-5 | 26 |
| 1-4 | 53 | 2-18 | 97 | 3-12 | 17 |
| 1-13 | 51 | 2-19 | 50 | 3-14 | 9 |
| 1-9 | 43 | 2-22 | 49 | 3-4 | 15 |
| 1-22 | 42 | 2-14 | 43 | 3-6 | 15 |
| 1-10 | 37 | 2-4 | 39 | 3-11 | 14 |
| 1-27 | 27 | 2-11 | 39 | 3-13 | 12 |
| 1-18 | 26 | 2-7 | 35 | 3-15 | 13 |
| 1-30 | 25 | 2-27 | 32 | 3-21 | 2 |
| 1-19 | 21 | 2-25 | 31 | 3-22 | 9 |
| 1-14 | 19 | 2-23 | 24 | 3-23 | 5 |
| 1-20 | 17 | 2-36 | 816 | 3-10 | 28 |
| 1-21 | 15 | 2-35 | 953 | 3-9 | 17 |
| 1-3 | 15 | 2-17 | 1187 | | |

[a] A capture ELISA was performed using the target rabbit anti-LOS antibody or an irrelevant rabbit antibody as a coating antigen, followed by incubating with individual phage clones selected from the biopanning process and then with an HRP anti-M 13 monoclonal antibody conjugate. The binding reactivity between the target antibody and the phage clones was evaluated by $OD_{405}$ values after addition of an ABTS substrate. Fifty-six positive phage clones were selected from fold rise of ELISA OD values as compared with that of the irrelevant antibody.

TABLE III

Four consensus peptide sequences derived from 22 positive clones

| Peptide[a] | Consensus Sequence | Clone No. | Positive/ Total (%) | Binding reactivity ($OD_{405}$)[b] |
|---|---|---|---|---|
| 1 | NMMRFTSQPPNN (SEQ OD NO:2) | 1-8, 2-9, 2-17, 2-35, 2-12, 1-25, 3-5, 3-12, 3-10 | 9/22 (41) | 0.40 |
| 2 | NMMNYIMDPRTH (SEQ ID NO:3) | 1-34, 1-23, 1-32 | 3/22 (14) | 2.52 |
| 3 | NMMKYISPPIFL (SEQ ID NO:4) | 1-14, 1-19, 1-27, 2-7, 2-16, 2-22, 2-23, 3-9, 3-14 | 9/22 (41) | 1.11 |
| 4 | NMMRFTELSTPS (SEQ ID NO:5) | 2-15 | 1/22 (5) | 0.99 |
| 5 | TLAHHKKPWILR (SEQ ID NO:10) | —[c] | — | 0.33 |

[a] Peptides 1 through 4 represent consensus peptide sequences from 22 clones selected from 56 positive phage clones (Table II). Peptide 5 represents a control peptide from an unrelated clone.
[b] The binding reactivity was determined by an ELISA, in which each peptide was covalently coupled to NucleoLink ™ strip as a coating antigen, followed by incubation with the target rabbit anti-LOS antibody. The binding reactivity of the synthetic peptides to the target antibody was evaluated by average $OD_{405}$ values of each duplicate sample after incubation with a goat anti-rabbit IgG alkaline phosphate conjugate, and then addition of a substrate.
[c] Not applicable.

Figure 1A:
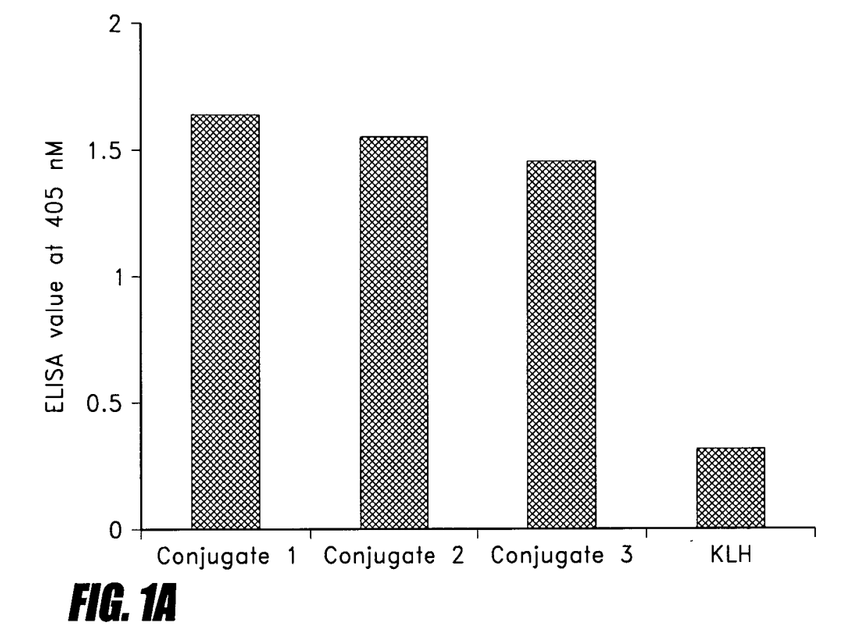
Figure 1B:
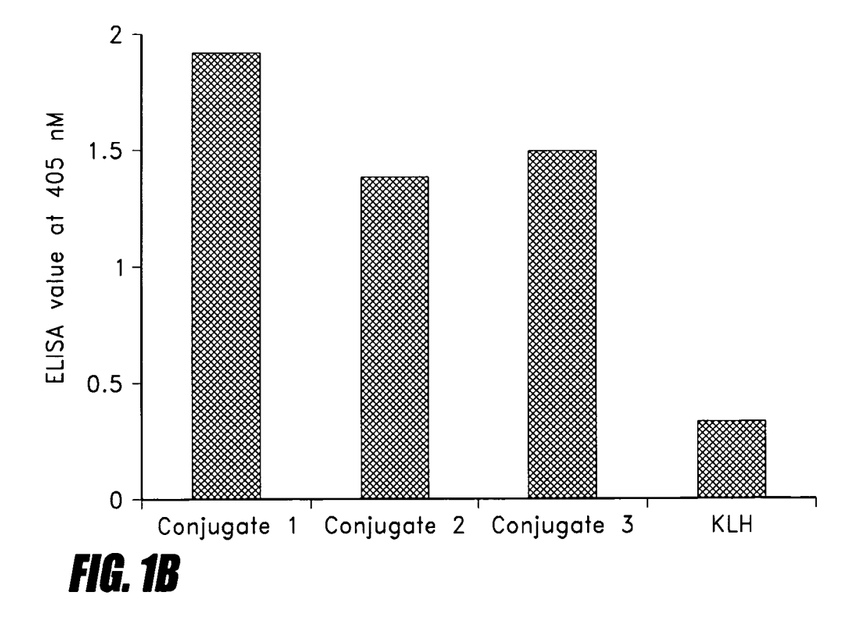

Binding Specificity of Synthetic Peptides and Synthetic Peptide Conjugates to Anti-LOS Antibodies Because the N terminus of each phage-displayed peptide was free during biopanning while its C terminus with GGGS fused to the phage membrane, four peptides and a negative peptide were synthesized with a spacer sequence (GGGS) added to each C terminus. Binding reactivity of peptides to target anti-LOS antibody was examined in an ELISA coated with the peptides (Table III). Peptides 2, 3, and 4 showed higher binding reactivity to the antibody than did peptide 1 or peptide 5 (controls). Therefore, peptides 2, 3, and 4 were further conjugated to KLH to form conjugates 1, 2, and 3 to enhance the immunogenicity of the peptides in vivo. FIG. 1 shows ELISA binding reactivity of the synthetic peptide conjugates to the rabbit anti-LOS antibody (target antibody) (FIG. 1A) or to a mouse monoclonal anti-LOS antibody 6347C11 (FIG. 1B). All three synthetic peptide conjugates bound strongly to either the rabbit or the mouse anti-LOS antibody with the best binding reactivity in conjugate 1. In contrast, the KLH alone showed lower binding reactivity relative to the conjugates.

Immunogenicity of the Synthetic Peptide Conjugates in Rabbits

Figure 2:
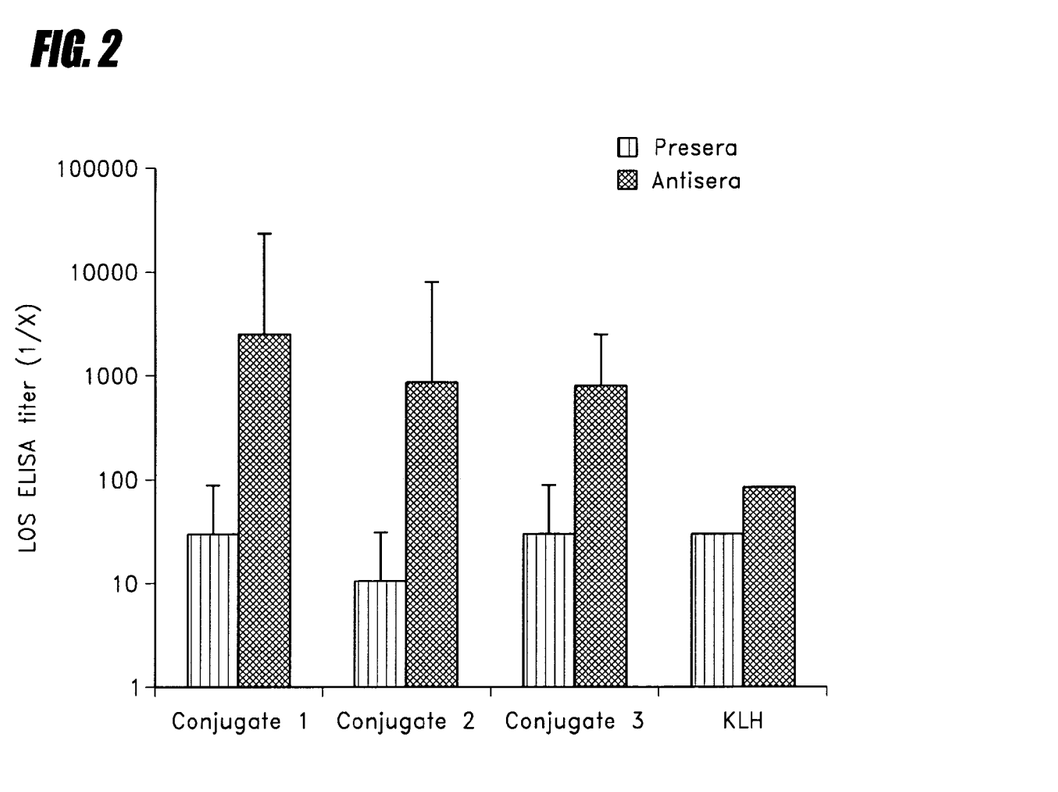

The immunogenicity of the synthetic peptide conjugates was evaluated in rabbits. All peptide conjugates elicited high levels of anti-peptide antibodies in rabbit serum as measured by ELISA using peptide-BSA as a coating antigen at a titer of $\geq 1:10,000$. Importantly, these rabbit antisera showed strong binding cross-reactivity with LOS as measured by the LOS ELISA using 9274 LOS as a coating antigen at average titers of 1:810 to 1:2430 (27- to 81-fold rise when compared with presera) (FIG. 2). Among the three conjugates, conjugate 1 elicited the highest anti-LOS antibody titers. In contrast, presera or antiserum elicited by KLH showed lower anti-LOS levels ($\leq 1:90$).

Passive Protection with Rabbit Antisera Elicited by Peptide Conjugates in a Mouse Challenge Model Balb/c mice were passively immunized with rabbit presera and antisera elicited by the peptide conjugates, whole cells, or dLOS-TT at 17 h prior to an aerosol challenge of NTHi strain 9274 (Table IV). Six hours post-challenge the mice were sacrificed to determine bacterial counts in lungs and passively transferred rabbit anti-LOS antibody levels in lungs and serum. The result indicated that 40% of rabbit antisera 7819, 7850, and 7822 elicited by conjugate 1, 2, or 3 (group 1, 4, or 6) significantly enhanced the bacterial clearance from mouse lungs by 35 to 44% when compared with that of preserum (group 8, $p<0.05$). Evidence of an antibody dose-dependent effect on bacterial clearance was found in conjugate 1 or 2. The 40% of rabbit antiserum 7819 or 7850 elicited by conjugate 1 or 2 significantly enhanced the bacterial clearance from mouse lungs by 32% when compared with that of 8% (group 1 versus 3 or group 4 versus 5, $p<0.05$). When rabbit antiserum 7819 was pretreated with 9274 LOS, it showed no enhanced bacterial clearance in the mouse lungs (group 2). Similar reductions of 41% and 50% were also obtained from two positive rabbit antisera elicited by dLOS-TT (group 9) and whole cells (group 10), respectively ($p<0.05$). There was no statistical significance for rabbit sera elicited by 3 peptide conjugates or by whole cells or dLOS-TT.

TABLE IV

Effect of passive immunization with rabbit antisera elicited by peptide conjugates on bacterial clearance in mouse lungs challenged with NTHi strain 9274[a]

| Group | Immunogen | Rabbit No. | Serum Conc. (%) | Bacterial recovery Mean ± SD (CFU/mouse) | Bacterial reduction (%)[b] |
|---|---|---|---|---|---|
| 1 | Conjugate 1 | 7819 | 40 | $1.9 \times 10^3 \pm 0.4$ | 44[c], 49[d], 32[e] |
| 2 | Conjugate 1 | 7819 | 40 + LOS | $3.7 \times 10^3 \pm 0.1$ | 9 |
| 3 | Conjugate 1 | 7819 | 8 | $2.8 \times 10^3 \pm 0.9$ | 18 |
| 4 | Conjugate 2 | 7850 | 40 | $1.9 \times 10^3 \pm 0.9$ | 44[c], 32[f] |
| 5 | Conjugate 2 | 7850 | 8 | $2.8 \times 10^3 \pm 0.8$ | 18 |
| 6 | Conjugate 3 | 7822 | 40 | $2.2 \times 10^3 \pm 0.5$ | 35[c] |
| 7 | Conjugate 3 | 7822 | 8 | $2.5 \times 10^5 \pm 1.1$ | 26 |
| 8 |  | Mixed | 40 | $3.4 \times 10^3 \pm 1.1$ | 0 |
| 9 | dLOS-TT | 105-2 | 40 | $2.0 \times 10^3 \pm 1.0$ | 41[c] |
| 10 | Whole cells | 44-2 | 40 | $1.7 \times 10^3 \pm 1.1$ | 50[c] |

[a]Ten mice in each group were immunized intraperitoneally with 40% or 8% rabbit pre- or post-sera elicited by peptide conjugates 17 h prior to an aerosol challenge with 10 ml of NTHi strain 9274 at a concentration of $10^8$ CFU/ml. Pre-serum was combined and injected only with 40% (Group 8). Two positive sera (Groups 9 and 10)included a rabbit serum elicited by strain 9274 whole cells and a rabbit serum elicited by dLOS-TT. Antiserum 7819 elicited by conjugate 1 was inhibited with 9274 LOS prior to the injection (Group 2). Six h postchallenge, mouse lungs were removed for bacterial counts.
[b]% of the first column based on group 8; other % noted when significant between two corresponding groups.
[c]$p < 0.05$, compared with group 8.
[d]$p < 0.05$, compared with group 2.
[e]$p < 0.05$, compared with group 3.
[f]$p < 0.05$, compared with group 5.

The passively transferred rabbit anti-LOS IgG levels in mouse lung homogenates and sera were measured and consistent with the injection dose of each rabbit serum. The correlation between bacterial counts in mouse lung homogenates and the antibody levels of rabbit IgG in the mouse lung homogenates or sera was analyzed in all mice except for two negative controls (inhibition group 2 and pre-serum group 8). The results indicated that there was negative correlation between the bacterial counts and the rabbit IgG levels in mouse lung homogenates (r=−0.47, P<0.0001) and sera (r=−0.45, P<0.001).

Discussion

Using phage display libraries, immunogenic peptide mimics of bacterial or fungal polysaccharides have been identified in *Candida albicans*, Group B streptococci, Group A meningococci, serotype 4 pneumococci, and *Shigella flexneri* (Table I). In the case of mimicry of bacterial endotoxin (LPS or LOS), the biggest advantage of using a peptide library is that the peptide mimetics are nontoxic and can be easily synthesized. However, attempts to identify mimotopes of bacterial endotoxins have met with only limited success. Peptide mimetics of *Brucella* LPS elicited weak anti-O-specific polysaccharide antibodies of the LPS while peptide mimetics of meningococcal LOS could elicit a 2 to 4-fold anti-LOS antibody in mice. Also, there is a successful report of mimic O-specific polysaccharide of *Shigella flexneri* LPS. Using a similar method but with an affinity purified rabbit anti-LOS polyclonal antibody, we have identified three mimotope peptides that mimic the LOS of NTHi through a 12-mer random peptide library.

A peptide mimic of carbohydrates is difficult to demonstrate, as there are only a few successful cases. Most are mimics of polysaccharides and the mechanisms of peptide mimetics are unclear although considerable progress has been made recently (Monzavi-Karbassi et al. 2002 *Trends Biotechnol* 20:207). We contemplate that it would be even more difficult to mimic a much smaller molecule of LOS (around 4 Kd), particularly for oligosaccharides with a big portion of hydrophobic lipid A molecule. The only attempt with meningococcal LOS mimetics resulted in weak to medium anti-LOS antibody in mice (Charalambous and Feavers 2000 *FEMS Microbiol Lett* 191:45). After trying a 12-mer-linear phage display peptide library, along with several modifications of the biopanning protocol, we were able to find 56 positive colonies from three individual biopanning processes. Twenty-two colonies were sequenced, resulting in four consensus sequences (mimotopes) with a possible motif of NMM (first three amino acids of SEQ ID NO: 1). We were unable to identify the repeating aromatic groups in our peptide mimetics found in peptides that are antigenic mimics of cryptococcal polysaccharide (Valadon et al. 1996 *J Mol Biol* 261:11), or that are immunogenic mimics of the Lewis Y antigen (Hoess et al. 1993 *Gene* 128:43) and meningococcal group C polysaccharide (Westerink et al. 1995 *PNAS USA* 92:4021). However, there is one aromatic group [phenylalanine (F) or tyrosine (Y)] at the fifth position of the N-terminus of each mimotope peptide. Furthermore, all mimotope peptides possess Arginine (R), Lysine (K), or Asparagine (N) at the fourth position of the N-terminus. These three residues can form hydrogen bonds in their side chains. The terminal NMM (first three amino acids of SEQ ID NO: 1) and the aromatic group along with R/K/N might play a major role in peptide binding to anti-LOS antibody as an antigen or for peptide eliciting LOS antibody as an immunogen in vivo. However, other amino acids may interfere with the LOS mimicry since peptide 1 did not show good antigenic mimic of the LOS (Table III). The precise interactions between the peptide mimotopes and the antibody paratopes may be revealed in the crystallographic structure of the antibody in complex with the mimotopes in future studies (Monzavi-Karbassi et al. 2002 *Trends Biotechnol* 20:207; Young et al. 1997 *J Mol Biol* 274:622; Glithero et al. 1999 *Immunity* 10:63).

Three synthetic mimotope peptides were shown to bind strongly to the target anti-LOS antibody and a monoclonal anti-LOS antibody in vitro. This indicates that the mimotope peptides share the antigenic mimicry of LOS. To evaluate the immunogenicity of the peptide mimotopes, rabbits were immunized with the peptide mimotope conjugates. High levels of anti-LOS antibodies were found in sera of immunized rabbits. Passive immunization of mice with the rabbit antisera showed protection against NTHi, comparable to that seen with rabbit antiserum against whole cells or dLOS-TT. The protection in most animals was in an antiserum dose-dependent pattern, and when this antiserum was pre-absorbed by LOS, the protection was inhibited. These data indicate that the mimotope peptides can also specifically mimic the LOS immunogenically and induce protective immune responses against NTHi.

The strategy we have reported is the basis for the development of a new type of anti-NTHi LOS vaccines. The use of peptide mimetics as vaccines offers several advantages in terms of safety, cost, stability, and relative ease of production. Needless to say, peptide mimetics have other potential advantages over LOS for immunogenicity, such as effective infant immunization, secondary immune response, and long-lasting immunity. In our case, this approach has the greatest utility since NTHi LOS is toxic and difficult to purify. To commercialize a licensable vaccine for human use, these proven peptides need to be conjugated to clinically acceptable carriers, such as TT, and conventionally tested in animal models, such as in active protection models of mouse pulmonary clearance and chinchilla OM by systemic or mucosal administration. Meanwhile, the peptides can be rationally designed with multivalent LOS mimotopes, multiple antigen peptides or to contain additional structures, including T helper cell epitopes and built-in adjuvants (Avila et al. 2001 *Parasite Immunol* 23:103; Marussig et al. 1997 *Int Immunol* 9:1817; Aoki et al. 1996 *Neurosci Lett* 205:11; Senpuku et al. 1996 *Immunology* 88:275). These applications are envisioned as further improving immunogenicity of these LOS mimotopes in vivo. In addition, DNA vaccines based on the LOS peptide mimotopes are contemplated to further extend the present strategy or open a new strategy for vaccine development (Lesinski et al. 2001 *Vaccine* 19:1717).

EXAMPLES

Example 1

Affinity Purification of an Antibody Specific for NTHi LOS

LOS was extracted from NTHi strain 9274 by phenol-water extraction and then column purification (Gu et al. 1996. *Infect Immun* 64:4047). A rabbit antiserum elicited by strain 9274 detoxified LOS-tetanus toxoid (TT) with bactericidal activity (Gu et al. 1996, supra) was purified through an LOS affinity column prepared by coupling the LOS to cyanogen bromide (CNBr)-activated Sepharose 4B (Pharmacia, Uppsala, Sweden). Two grams of Sepharose 4B was suspended in 1 mM HCl, transferred into a sintered glass filter, and washed with 1 mM HCl for 15 min. The washed 4B gel was mixed with 10 ml of coupling buffer (0.1 M NaHCO$_3$, 0.5 M NaCl, pH 8.3) containing 20 mg of LOS in a tube and rotated overnight at 4° C. After washing with the coupling buffer, the gel was dried, suspended, and blocked with 0.1 M Tris-HCl (pH 8) for 2 h, followed by washing with 0.1 M acetate buffer (pH 4) and 0.5 M NaCl and then with 0.1 M Tris-HCl (pH 8) and 0.5 M NaCl. After repeating the washing step three times, the gel was washed with the coupling buffer, then 0.5% bovine serum albumin (BSA) in phosphate-buffered saline (PBS, pH 7.4), and suspended in 0.5% BSA for 2 h. An LOS affinity column was prepared after washing with PBS and loaded with the rabbit antiserum. The column was washed with 0.5% BSA and PBS and eluted with 3.5 M $MgCl_2$. Fractions with a protein peak at $OD_{280}$ value, designated as the target anti-LOS antibody, were collected and immediately dialyzed against PBS at 4° C. The protein content of the antibody was determined with a Micro BCA kit (Pierce, Rockford, Ill.). The binding reactivity of the antibody to the LOS was tested with an LOS enzyme-linked immunosorbent assay (ELISA) (Gu et al. 1996, supra) using 1 µg/well of LOS as a coating antigen in a 96-well Nunc-Immuno plate (MaxiSorp surface; Nalge Nunc International, Roskilde, Denmark). The plate was then incubated with 1.4 µg/well of the target anti-LOS or an irrelevant rabbit IgG antibody (Southern Biotechnology Associates, Birmingham, Ala.), followed by a goat anti-rabbit IgG (whole molecule) alkaline phosphatase conjugate at 1:3,500 (Sigma-Aldrich, St. Louis, Mo.). ELISA OD values were obtained with a microplate autoreader (EL309, Bio-Tek instruments, Winooski, Vt.) at $A_{405}$ after addition of p-nitrophenyl phosphate for 30 min. This affinity-purified rabbit anti-LOS antibody was used as the target antibody in each of the biopanning round.

Example 2

Generation of Polyclonal Antibody

Bacterial growth and LOS purification. NTHi 9274, isolated from middle ear fluid removed from a patient with OM, was provided by M. A. Apicella, University of Iowa. The strain was grown on chocolate agar at 37° C. under 5% $CO_2$ for 8 h and transferred to 200 ml of 3% brain heart infusion medium (Difco Laboratories, Detroit, Mich.) containing NAD (5 µg/ml) and hemin (2 µg/ml) (Sigma Chemical Co., St. Louis, Mo.) in a 500-ml bottle. The bottle was incubated at 150 rpm in an incubator shaker (model G-25; New Brunswick Scientific, Co., Edison, N.J.) at 37° C. overnight. The culture was transferred to five 2.8-liter baffled Fembach flasks, each of which contained 1.4 liters of the same medium. The flasks were shaken at 140 rpm and maintained at 37° C. for 24 h. The culture was centrifuged at 15,000×g at 4° C. for 30 min to separate the cells and the supernatant. LOS was purified from cells by a modified phenol-water extraction (Gu et al. 1995 *Infect Immun* 63:4115-4120) and from the culture supernatant by gel filtration (Gu et al. 1991 *Anal Biochem* 196:311-318). The protein and nucleic acid contents of both purified LOSs were less than 1% (Smith et al. 1985 *Anal Biochem* 156:220-222; Warburg and Christian. 1942 *Biochem Z* 310: 384-421).

Detoxification of LOS. Anhydrous hydrazine treatment of lipopolysaccharides (LPSs) under mild condition removes esterified fatty acids from lipid A (Gupta et al. 1992 *Infect Immun* 60:3201-3208). LOS (160 mg), each lot, was dried over $P_2O_5$ for 3 days, suspended in 16 ml of anhydrous hydrazine (Sigma-Aldrich), and incubated at 37° C. for 2 h with mixing every 15 min. This suspension was cooled on ice and added dropwise to cold acetone in an ice bath until a precipitate formed ($\geq$90% acetone). The mixture was centrifuged at 5,000×g at 5° C. for 30 min. The pellet was washed twice with cold acetone and dissolved in pyrogen-free water at a final concentration of 20 mg/mi. The reaction mixture was ultracentrifuged at 150,000×g at 5° C. for 3 h. The supernatant was freeze dried and passed through a column (1.6 by 90 cm) of Sephadex G-50 (Pharmacia LKB Biotechnology, Uppsala, Sweden), eluted with 25 mM ammonium acetate, and monitored with a differential refractometer (R-400; Waters, Milford, Mass.). The eluate was assayed for carbohydrate by the phenol-sulfuric acid method (Dubois et al. 1956 *Anal Biochem* 28:250-256). The carbohydrate-containing fractions were pooled, freeze-dried three times to remove the salt, and designated dLOS. The yields of the dLOS from three lots ranged from 48 to 55% by weight. For all material and reagent preparations, glassware was baked and pyrogen-free water was used.

Derivatization of dLOS. Adipic acid dihydrazide (ADH) (Aldrich Chemical Co., Milwaukee, Wis.) was bound to the carboxyl group of the KDO moiety of the dLOS to form adipic hydrazide (AH)-dLOS derivatives with 1-ethyl-3-(3-dimethylaminopropyl)carbodiimide HCl (EDC) and N-hydroxysulfosuccinimide (Pierce) (Gu et al. 1993 *Infect Immun* 61:1873-1880; Staros et al. 1986 *Anal Biochem* 156:220-222). DLOS (70 mg) was dissolved in 7 ml of 345 mM ADH (the molar ratio of ADH to LOS is ~100:1 based on an estimated 3,000 $M_r$ for dLOS) (Gibon et al. 1993 *J Bacteriol* 175:2702-2712; Helander et al. 1988 *Eur J Biochem* 177:483-492). N-Hydroxysulfosuccinimide was added to a concentration of 8 mM, the pH was adjusted to 4.8 with 1 M HCl, and EDC was added to a concentration of 0.1 M. The reaction mixture was stirred and maintained at pH 4.8±0.2 with 1 M HCl for 3 h at room temperature. It was adjusted to pH 7.0 with NaOH and passed through the G-50 column as described above. The eluate was assayed for carbohydrate and for AH by a modification of a previously described method (Kemp and Morgan. 1986 *J Immunol Methods* 94:65-72) by measuring the $A_{490}$ of AH groups. The peaks containing both carbohydrate and AH were pooled, freeze-dried three times to remove the salt, and designated AH-dLOS. AH-dLOS was measured for its composition with dLOS and ADH as standards (Dubois et al. 1956 *Anal Biochem* 28:250-256; Kemp and Morgan. 1986 *J Immunol Methods* 94:65-72).

Conjugation of AH-dLOS to TT. TT was obtained from Connaught Laboratories, Inc., Swiftwater, Pa. AH-dLOS was coupled to carboxyl groups on TT at pH 5.6 with EDC. AH-dLOS (20 mg) was dissolved in 2 ml of water and mixed with 10 mg of TT (5.9 mg/ml). The molar ratio of AH-dLOS to TT ($M_r$, 150,000) was ~100:1. The pH was adjusted to 5.6 with 0.1 M HCl, and EDC was added to a concentration of 0.1 M. The reaction mixture was stirred for 1 to 3 h at room temperature; the pH was maintained at 5.6±0.2 with 0.1 M HCl. The reaction mixture was adjusted to pH 7.0, centrifuged at 1,000×g for 10 min, and passed through a column (1.6 by 90 cm) of Sephacryl S-300 in 0.9% NaCl. Peaks that contained both protein and carbohydrate were pooled and designated dLOS-TT. The conjugate was analyzed for its composition of carbohydrate and protein with dLOS and bovine serum albumin (BSA) as standards (Dubois et al. 1956 *Anal Biochem* 28:250-256; Smith et al. 1985 *Anal Biochem* 150:76-85).

Inoculation of Rabbits. Female New Zealand White rabbits, weighing 2 to 3 kg (two or three per group), were given a total of two subcutaneous and intramuscular injections at 4-week intervals with 50 µg of conjugates (carbohydrate) in 1 ml of 0.9% NaCl with Ribi-700 adjuvant (containing 250 µg of monophosphoryl lipid A and 250 µg of synthetic trehalose dicorynomycolate) and bled 2 weeks after the first injection and 11 to 14 days after the second injection.

Example 3

Biopanning to Select Phage-Display Peptides that Mimic NTHi LOS

A Ph.D.-12™ Phage Display Peptide Library was purchased from New England BioLabs Inc. (Beverly, Mass.) with a concentration of $1.5 \times 10^{13}$ pfu/ml and complexity at $2.7 \times 10^9$ transformants. A biopanning protocol was executed following manufacturer's instruction (Version 2.5) by incubating the library of phage display peptides with a 96-well Nunc-Immuno plate (Nalge Nunc International) coated with the affinity-purified target antibody (2.5 µg in PBS/100 µl/well), washing away the unbound phage and eluting the bound phage. The eluted phage was then amplified and taken through additional cycles of bio-panning and amplification to enrich the phages with the highest affinity. After 3 rounds, an individual clone was selected, amplified and characterized by a capture ELISA with the target anti-LOS antibody as a coating antibody. To overcome the difficulty in mimicking saccharide epitopes after several unsuccessful trials, three major modifications were made for each bio-panning round. The library was absorbed with an irrelevant rabbit IgG at 3.75 µg in PBS/150 µl/well at room temperature (RT) for 1 h with agitation before incubation in another well coated with anti-LOS antibody. Before the eluting step with TBS [50 mM Tris-HCl (pH 7.5) and 150 mM NaCl] containing NTHi 9274 LOS (80 µg/150 µl/well), the well was eluted with the TBS containing the irrelevant antibody (10 µg/200 µl/well). For amplification of the selected individual clone, we made 1 ml of host bacteria in LB (Luria Bertani) culture ($OD_{600}=0.5$) with each selected plaque in 14-ml Falcon tube (Becton Dickinson Labware, Franklin Lakes, N.J.) instead of making 20 ml of host bacteria in LB culture in a 250-ml Erlenmeyer flask. The first two steps removed nonspecific binding phages while the third step retained high affinity binding clones and reduced mutants.

Example 4

ELISA for Screening Positive Clones

A capture ELISA was performed for screening the positive phage clones described by the instructions of the peptide library kit with minor modifications. Briefly, the supernatant of the 1 ml amplified culture from each clone was used as the testing sample. A 96-well Nunc-Immuno™ plate was coated with the target anti-LOS antibody or the irrelevant antibody (8 µg/ml in PBS) at 110 µl/well, overnight at 4° C. The plate was blocked with 3% BSA in TBS at 300 µl/well for 2 h at 4° C., followed by adding each duplicate sample suspended with 0.1% Tween 20 in TBS at 100 µl/well for 2 h at RT with agitation. An HRP anti-M13 monoclonal antibody conjugate (Pharmacia) at 1:5,000 in 3% BSA in TBS was added for 1 h at RT under agitation. A washing buffer with 0.5% Tween 20 in TBS was used between steps, each for 8-10 times. The binding reactivity between the anti-LOS antibody and the selected phage clones was evaluated by $OD_{405}$ values at 30 min at RT after addition of an ABTS (Sigma-Aldrich) substrate solution. The positive clones should show blue-green color.

Example 5

DNA Sequencing on Positive Clones

To prepare DNA sequencing templates, each 700 µl of the supernatant of the 1 ml amplified culture was transferred into a 1.5 ml tube and 300 µl of polyethylene glycol (PEG)/NaCl (20% PEG-8000, 2.5 M NaCl) was added. The mixture was kept at RT for 10 min, spun, and the supernatant was discarded. The pellet was suspended in 100 µl iodide buffer [10 mM Tris-HCl (pH 8), 1 mM EDTA, 4 M NaI], followed by the addition of 250 µl of 70% ethanol. The mixture was kept at RT for 10 min, spun, and the supernatant was discarded. The pellet was washed with the ethanol and suspended in 30 µl of TE buffer [10 mM Tris-HCl (pH 8), 1 mM EDTA] for DNA sequencing (Veritas, Inc., Rockville, Md.). Peptide sequences were deduced from DNA sequences.

Example 6

Synthetic Peptides and their Binding Reactivity to the Target Anti-LOS Antibody

Four peptides were synthesized with a spacer (GGGS) at each C-terminus (Genemed Synthesis, Inc., San Francisco, Calif.). Binding reactivity of the synthetic peptides to the target anti-LOS antibody was tested with a peptide ELISA using Nunc NucleoLink™ Strips (Fisher Scientific, Pittsburgh, Pa.). Following the instructions of the product with modifications, the strips were coated covalently with its amino groups to the C-terminal carboxyl groups of the synthetic peptides by a coupling reagent, [1-Ethyl-3-(3-dimethylaminopropyl) carbodiimide HCl] (EDC, Pierce). Briefly, peptides and 0.1 M 1-methyl-imidazole (MeIm) (Sigma-Aldrich) at pH 7 were pre-cooled on ice, and a 100 µl of individual peptide solution with 5 µg of peptide in 10 mM MeIm was prepared in a well of strips on ice. This peptide solution (75 µl) was mixed with 25 µl of freshly prepared 0.2 M EDC in 10 mM MeIm in another well of the strips. The strips were sealed and incubated at 50° C. for 5 h. After removing the reaction mixture, the strips were soaked with washing buffer (freshly prepared 0.25% SDS in 0.4 N NaOH and warmed at 50° C.) for 5 min and emptied. This step was performed for three times, followed by another three washings without the 5-min soaking. After removing the washing buffer, the strips was washed thoroughly with deionized water. The following steps were the same as described in the LOS ELISA (Gu et al. 1996 *Infect Immun* 64:4047). After blocking with 1% BSA in PBS, the target anti-LOS antibody was added in the amount of 0.4 µg/well followed by a goat anti-rabbit IgG alkaline phosphatase conjugate. The binding reactivity of the synthetic peptides to the target anti-LOS antibody was evaluated by $OD_{405}$ values at 30 min after adding a substrate.

Example 7

Synthetic Peptide Conjugates and their Antigenicity in vitro and Immunogenicity in Rabbits Three peptide-KLH conjugates were synthesized covalently using Sulfosuccinimidyl 4-(N-Maleimido-methyl) Cyclohexane-1-Carboxylate (SMCC) as a linker for the coupling reaction (Genemed Synthesis). A peptide spacer, GGGSC (SEQ ID NO: 11), was introduced at each peptide's C-terminus and was conjugated to KLH. The ratio of the synthetic peptides to KLH was about 20% by weight. Antigenicity of these conjugates in vitro was examined in ELISA using conjugates or KLH as coating antigens (2 μg/well in 0.1 M Tris buffer, pH 8) and the target rabbit anti-LOS antibody (0.1 μg/well). The conjugates (5 μg/well) were also tested for their binding reactivity with a mouse bactericidal monoclonal anti-LOS antibody 6347C 11 at 1:500 of ascites (Ueyama et al. 1999 *Clin Diag Lab Immunol* 6:96). Other steps of this ELISA were the same as described in the LOS ELISA except goat anti-mouse IgM (μ-chain specific) alkaline phosphatase conjugate (Sigma-Aldrich) was used at 1:3,500 for detecting the monoclonal antibody. In addition, each peptide was also conjugated with BSA as a coating antigen (10 μg/well) for the following ELISA to detect rabbit antibodies against peptides without interference from the existing KLH antibodies.

To study the immunogenicity of the peptide conjugates, New Zealand White female rabbits 3.5 months of age, two for each group, were subcutaneously immunized with 500 μg of each conjugate (approximately 100 μg of peptide content) suspended in 0.5 ml of PBS (Genemed Synthesis). The immunization was repeated three times with 20-day intervals. Each injection volume was 1 ml in which the first dose was mixed with 0.5 ml of complete Freund adjuvant, and the boosters with 0.5 ml of incomplete Freund adjuvant. A control rabbit immunized with 500 mg KLH along with the above adjuvants was also included. Blood samples were collected before and 10 days after the fourth injection to detect serum antibodies against synthetic peptides or NTHi LOS in ELISA using peptide-BSA conjugates or LOS as coating antigens (Gu et al. 1996 supra). The ELISA was performed by incubation with the rabbit sera, followed by addition of a goat anti-rabbit IgG alkaline phosphatase conjugate. The antibody endpoint titier was defined as the highest dilution of a serum sample giving an OD value greater than 0.5 at $A_{405}$ after addition of a substrate for 20 min.

Example 8

Passive Protection with Rabbit Antisera Elicited by Peptide Conjugates in a Mouse Model The passive protection study was performed in accordance with National Institutes of Health guidelines under Animal Study Protocol #1009-01. Female Balb/c mice at the age of 8 weeks were immunized intraperitoneally with 1 ml of rabbit pre-sera (40%) or post-sera (8%) elicited by peptide-KLH conjugates (rabbit number 7819, conjugate 1; 7850, conjugate 2; and 7822, conjugate 3) diluted in normal saline 17 h prior to NTHi challenge. Pre-sera were pooled and injected only with 40% for the bacterial challenge. Two positive antisera included a rabbit antiserum elicited by NTHi 9274 whole cells and a rabbit antiserum elicited by NTHi 9274 dLOS-TT. Antiserum 7819 elicited by conjugate 1 was also pretreated with 9274 LOS to determine if the antibodies elicited by the peptide conjugate could be removed by the LOS antigen. The 40% serum 7819 was incubated with 9274 LOS (100 μg/ml) at 37° C. for 1 h and then at 4° C. overnight with gentle rotation. The pre-absorbed antiserum along with other diluted sera were low centrifuged and sterile filtered prior to use. Ten mice as a group were used for each rabbit serum, followed by an aerosol challenge in an Inhalation Exposure System (Glas-Col, Terre Haute, Ind.), in which freshly harvested strain 9274 bacteria in log-phase growth were suspended [$10^8$ cfu (colony forming unit)/ml] in 10 ml of PBS containing 0.1% gelatin, 0.15 mM $CaCl_2$ and 0.5 mM $MgCl_2$ (PBSG) as the challenge bacteria (Hu et al. 2000 *Vaccine* 18:799). Six hours postchallenge, blood samples were collected for antibody measurements and mouse lungs removed for bacterial counts and antibody measurements. The lungs were homogenized in 10 ml of PBSG for 1 min using a tissue homogenizer. Each homogenate was diluted serially in PBS and 50 μl of the homogenate and the diluted samples were plated on chocolate agar plates. The plates were incubated at 37° C. with 5% $CO_2$ overnight, and the bacterial colonies were counted. The minimal detection level of bacterial counts was 200 cfu per mouse. Both serum and lung homogenate samples were also detected for rabbit anti-LOS IgG passively immunized in mice prior to the challenge by the LOS ELISA as described above (Gu et al. 1996 *Infect Immun* 64:4047).

Example 9

Statistical Analysis

Bacterial colonies were expressed as the mean CFU of an independent observation±standard deviation (S.D.). Significance was determined using Mann-Whitney non-parametric analysis. Linear regression and correlation analysis was done between the bacterial count in each mouse lung and its corresponding IgG level in serum or lung homogenate.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An isolated polypeptide up to 25 amino acids in length, wherein said polypeptide comprises a dodecapeptide having a sequence selected from the group consisting of NMMRFTSQPPNN (SEQ. ID. NO. 2), NMMNYIMDPRTH (SEQ. ID. NO. 3), NMMKYISPPIFL (SEQ. ID. NO. 4), and NMMRFTELSTPS (SEQ. ID. NO. 5).

2. The isolated polypeptide according to claim 1, wherein the polypeptide consists of the sequence NMMRFTSQPPNN (SEQ. ID. NO. 2).

3. The isolated polypeptide according to claim 1, wherein the polypeptide consists of the sequence NMMNYIMDPRTH (SEQ. ID. NO. 3).

4. The isolated polypeptide according to claim 1, wherein polypeptide consists of the sequence NMMKYISPPIFL (SEQ. ID. NO. 4).

5. The isolated polypeptide according to claim 1, wherein the polypeptide consists of the sequence NMMRFTELSTPS (SEQ. ID. NO. 5).

6. An isolated nontypeable Haemophilus influenzae lipooligosaccharide (NTHi LOS) mimotope comprising the isolated polypeptide of claim 2 and a carrier wherein the carrier is conjugated to the polypeptide.

7. An isolated nontypeable Haemophilus influenzae lipooligosaccharide (NTHi LOS) mimotope comprising the isolated polypeptide of claim 3 and a carrier wherein the carrier is conjugated to the polypeptide.

8. An isolated nontypeable Haemophilus influenzae lipooligosaccharide (NTHi LOS) mimotope comprising the isolated polypeptide of claim 4 and a carrier wherein the carrier is conjugated to the polypeptide.

9. An isolated nontypeable Haemophilus influenzae lipooligosaccharide (NTHi LOS) mimotope comprising the isolated polypeptide of claim 5 and a carrier wherein the carrier is conjugated to the polypeptide.

10. The isolated mimotope according to claim 6, wherein the carrier comprises an immunogenic protein.

11. The isolated mimotope according to claim 7, wherein the carrier comprises an immunogenic protein.

12. The isolated mimotope according to claim 8, wherein the carrier comprises an immunogenic protein.

13. The isolated mimotope according to claim 9, wherein the carrier comprises an immunogenic protein.

14. An immunogenic composition comprising the isolated mimotope according to claim 6 and an adjuvant.

15. An immunogenic composition comprising the isolated mimotope according to claim 7 and an adjuvant.

16. An immunogenic composition comprising the isolated mimotope according to claim 8 and an adjuvant.

17. An immunogenic composition comprising the isolated mimotope according to claim 9 and an adjuvant.

* * * * *